United States Patent [19]

McIntyre et al.

[11] Patent Number: 4,950,329

[45] Date of Patent: Aug. 21, 1990

[54] WOOD PRESERVATIVE COMPOSITION AND METHOD OF TREATING WOOD WITH SAME

[75] Inventors: Craig R. McIntyre, Pittsburgh; Eugene A. Pasek, Monroeville, both of Pa.

[73] Assignee: Hickson Corporation, Atlanta, Ga.

[21] Appl. No.: 255,742

[22] Filed: Oct. 11, 1988

[51] Int. Cl.$^5$ ................................................ C09D 5/14
[52] U.S. Cl. ................................. 106/15.05; 427/397; 427/440; 427/442
[58] Field of Search ........................... 106/18.29–18.31, 106/15.05; 252/312; 427/397, 440

[56] References Cited

U.S. PATENT DOCUMENTS

| | | | |
|---|---|---|---|
| 3,378,381 | 4/1968 | Draganov | 106/15.05 |
| 3,832,463 | 8/1974 | Nicholson | 424/131 |
| 4,313,976 | 2/1982 | Leach | 427/297 |
| 4,439,558 | 3/1984 | Tamosauskas et al. | 106/243 |
| 4,656,060 | 4/1987 | Krzyzewski | 106/18 |
| 4,783,221 | 11/1988 | Grove | 106/18.22 |
| 4,788,001 | 11/1988 | Narula | 252/312 |

OTHER PUBLICATIONS

Distribution and Effectiveness in Pinus Sp of a Water Repellant Additive for Water Borne Wood Preservatives, Levi et al., Forest Products Journal, vol. 20, no. 11, pp. 32–37 (Nov. 1970).
"Emulsion Addivites: A New Concept in Copper–Chrome–Arsenate Treatment," pp. 69–93. Record of Eighteenth Annual Convention-B. W. P. A.
GAF IGEPAL CO. Nonionic Surfactants Product Literature (1976, 1982).

*Primary Examiner*—Theodore Morris
*Attorney, Agent, or Firm*—Herbert J. Zeh, Jr.

[57] ABSTRACT

A wood preservative composition comprises a wood preservative such as a chromated copper arsenate-oil emulsion or an ammoniacal copper arsenate emulsion having about 0.1 to 15 percent chromated copper arsenate, ammoniacal copper arsenate, or ammoniacal copper zinc arsenate, about 1 to 20 percent oil and about 0.3 to 2.5 percent (based on total final emulsion) surfactant material. The first surfactant preferably has a hydrophilic lipophilic balance of about 7 to 9.5 and a second surfactant has a hydrophilic lipophilic balance of about 15 to 20. It is preferred that the first surfactant have an ethoxyl mole ratio less than about 5 and that the second surfactant have a mole ratio greater than about 15. The surfactant material may be composed of a first surfactant having an average mole ratio of about 1 to 5 and a second surfactant having an average mole ratio of about 20 to 100. The composition is storage stable for extended periods and provides a number of beneficial properties for wood products. A preferred group of surfactants for use in the present invention are ethoxylated alkylphenols or ethoxylated alkyl alcohols. A related method includes establishing an emulsion in oil of a first surfactant having an ethoxyl mole ratio less than about 5 and establishing in water a second surfactant having a mole ratio greater than about 15. The solutions are admixed and about 0.1 to 15 percent chromated copper arsenate, ammoniacal copper arsenate, or ammoniacal copper zinc arsenate is introduced into the mixed emulsions. The first and second surfactants may be emulsified in the oil which is subsequently admixed with the water, if desired. The chromated copper arsenate, ammoniacal copper arsenate or ammoniacal copper zinc arsenate bearing mixed emulsions are then introduced into wood. The composition and method are particularly useful with respect to wood products which will be used over prolonged periods in outdoor or other potentially hostile environments and are particulalry useful for utility poles, building products, and marine applications.

18 Claims, No Drawings

WOOD PRESERVATIVE COMPOSITION AND METHOD OF TREATING WOOD WITH SAME

BACKGROUND OF THE INVENTION

1. Field of the Invention

This invention relates to a preservative composition which improves wood properties and to a process of treating wood with such a composition.

2. Description of the Prior Art

It has long been known that wood, if not properly treated and exposed to outdoor conditions over prolonged periods of time will tend to deteriorate. Such deterioration may be caused by rotting under the influence of moisture, insect attack, biological degradation or other means.

Various means have been developed to protect wood from deterioration. Simple surface treatment such as painting and/or impregnation of various preservatives into the wood have long been known.

Among the known types of wood preservatives are oily preservatives such as creosote or pentachlorophenol in heavy oil as well as water borne copper-chromearsenate preservatives as well as ammoniacal copper arsenate (ACA). See generally, *Distribution and Effectiveness in Pinus Sp of a Water-Repellent Additive for Water Borne Wood Preservatives*, Levi et al., Forest Products Journal, Vol. 20, No. 11, pp. 32–37 (Nov., 1970).

It has been known to treat wood with chromated copper arsenate (CCA) emulsions, including CCA-oil emulsions, in order to resist decay of the wood, insect attack and biological degradation of the same.

It has also been known to use such treatments in wood products, such as utility poles, which are intended for long term use in outdoor environments.

It has also been suggested to employ copper-chromearsenate treatment solutions having a self-dispersing additive which is said to consist of a hydrophobic constituent which is a blend of long-chain petroleum hydrocarbon fractions, a surface active agent which is said to be a blend of non-ionic surfactants, and a petroleum-distillate solvent. See "Emulsion Additives: A New Concept in Copper-Chrome-Arsenate Treatment" pp. 69–93.

It has also been known to suggest the use of nonylphenyl ethoxylates as in preservative compositions for wood. See United States Patent Application No. 713,386. See also GAF IGEPAL CO Nonionic Surfactants product literature.

U.S. Pat. No. 3,832,463 discloses a water in oil wood preservative employing hydrophobic wax. It also discloses the use of a non-ionic surface active agent having an HLB value between 7 and 11.

U.S. Pat. No. 4,313,976 discloses the use of a coloring agent in the form of an organic dye in a wood preservative material.

U.S. Pat. No. 3,378,381 discloses an emulsion for preserving and fireproofing wood. A non-reactive preservative (chlorinated phenol) is employed in the oil phase. It teaches the use of a quantity of oil equal to or greater than the amount of water in the emulsion. It discloses incorporating of preservatives in the aqueous phase, but provides an emulsion system which would tend to cause rapid and extensive sludge formation as the chromate and arsenate type materials would react with the lignin sulfonate surfactants which he discloses.

It has been known that chromated copper arsenate may be used beneficially in the preservation of wood through resisting decay, insect attack and other forms of biological degradation. While this material is environmentally safe, it has presented problems. It is known that highly charged anions and cations serve to break emulsions. As fresh aqueous solutions of chromated copper arsenate contain such ions as $HCrO_4^-$, $CrO_4^{2-}$, $Cu^{2+}$, $H_2AsO_4$, $HAsO_4^{2-}$ and $AsO_4^{3-}$. Emulsion of such ions will have poor stability. Also, the chromated copper arsenate solutions are highly acidic tending to have a pH in the range of about 1.8 to 2.2 and are oxidative in nature. As a result, emulsifiers which are unstable in acid or which can be readily oxidized may not be used with such solutions.

European Pat. No. 0043035 discloses a water in oil emulsion which employs pigments as colorants.

U.S. Patent Application Ser. No. 941,754 discloses a wood preservation system which includes bringing together under the influence of ultra high shear emulsifying water and oil phases wherein the emulsion has an emulsifying agent. One end of the emulsifying agent reacts with the oil while the other end reacts with the water. The emulsifying agents are said to be ethoxylated amines or fatty amines with ethoxylated diamines being preferred. The use of a rhelogy structuring agent which is a high mole ratio, water soluble polymer of ethylene oxide is also disclosed. Ultra high shear equipment is required in order to make this emulsion.

In spite of these prior art disclosures, there remains a very real and substantial need for an effective wood preservative composition which will provide a wide variety of desirable properties for the wood while being storage stable and, more specifically, there is need for such a composition which contain chromated copper arsenate and an oil emulsion.

SUMMARY OF THE INVENTION

The present invention employs an emulsion made from oil and water emulsions having a low mole ratio oil soluble adduct with a high mole ratio water soluble adduct.

The present invention has met the above-described need by providing a wood preservative composition which contains about 0.1 to 15 percent chromated copper arsenate, ammoniacal copper arsenate (ACA), or ammoniacal copper zinc arsenate (ACZA), about 1 to 20 percent oil and about 3.0 to 25 percent (based on oil weight) total surfactant material. The surfactant material is preferably composed of a first surfactant having an average mole ratio of about 1 to 5 moles of ethoxyl groups to moles of alkylphenol or alcohol and a second surfactant having an average mole ratio of about 15 to 100. The first surfactant preferably has a hydrophilic lipophilic balance of about 7 to 11 and a second surfactant has a hydrophilic lipophilic balance of about 15 to 20. The preferred hydrophilic lipophilic balance of the combined surfactants is about 11 to 12. A preferred group of surfactants for use in the present invention are ethoxylated alkylphenols or ethoxylated alkyl alcohols.

In the method of the invention a solution is established with a first surfactant having a mole ratio less than about 5 in oil and a second solution having a second surfactant having a mole ratio greater than about 15, preferably greater than about 20 and most preferably greater than about 50, is established in water. The solutions are admixed to form an emulsion and about 0.1 to 15 percent chromated copper arsenate or ammoniacal copper arsenate (ACA) is introduced into the admixed emulsions. The material is then impregnated into wood. This impregnation may be accomplished by conventional means.

It is an object of the present invention to provide a wood preservative composition which has substantial storage stability and good treatability.

It is another object of the present invention to provide such a composition which may be employed using conventional apparatus and methods.

It is a further object of the invention to provide such a composition and a process of using the same in treating wood which will provide a durable wood product having good workability, and high dimensional stability.

It is a further object of the invention to employ the composition and method in treating utility poles.

It is a further object of the present invention to provide such a composition and wood treatment method which will produce a utility pole having improved climbability that resists splitting, warping and checking.

It is a further object of the present invention to provide a wood product which has desired leach resistance, water repellency and hardness.

It is another object of this invention to provide such a composition which has an oil constituent which has high viscosity and low volatility and resists undesired oil migration within wood.

It is a further object of the invention to provide such a composition which is economical to employ and will resist undesired oxidation by chromium (VI).

These and other objects of the invention will be more fully understood from the following description of the invention.

DESCRIPTION OF THE PREFERRED EMBODIMENTS

Unless specifically indicated to the contrary herein all references to percentages shall be deemed to be weight percentages based upon the entire weight of the final emulsion.

The term "storage stable" as used herein shall mean that the emulsion remains stable without visual indication of meaningful separation of the emulsified materials. The wood preservative composition of this invention will remain storage stable for a minimum of one day and preferably greater than four days.

In general, the present invention contemplates the use of multiple surfactants of a specific type in the creation of a chromated copper arsenate-oil emulsion or ammoniacal copper arsenate-oil emulsion which will provide substantially improved properties for wood products with particular emphasis on those wood products which are adapted for long term use out of doors or in other hostile environments. The CCA is a chemically reactive preservative which is employed in the aqueous phase. It is contemplated that a first solution consisting of a first surfactant and oil will be created and a second solution consisting of a second surfactant and water will be independently created with the two solutions subsequently being admixed and chromated copper arsenate, ammoniacal copper arsenate, or ammoniacal copper zinc arsenate being added to the resulting admixed emulsions.

It is preferred that the oil employed in the present invention be a highly refined oil having a high viscosity, kin., $m^2/S(cSt)$ at 37.8° C. (100° F.) and low flash point or volatility. It is preferred that the viscosity of the oil prior to creation of the oil containing emulsion be about 2 to 100 and that the flash point be greater than about 150° F.

Among the oils found particularly well suited to the present invention are naphthenic oil, paraffinic oil, No. 2 fuel oil, lubricating oil and mineral oil.

The oil will generally be employed in an amount of about 1 to 20 percent by weight of the final emulsion, i.e. total chromated copper arsenate bearing mixed oil and water emulsions. It has generally been found that the preferred amount of oil is about 1 to 6 percent. As it has been found that the amount of final emulsion or final wood treatment composition retained within wood actually is reduced once the oil concentration exceeds about 6 percent, such usage would involve increased expense due to the use of additional oil while producing reduced properties.

It is desirable for certain uses, such as use in utility poles, that the wood retain moisture in order to achieve a relatively soft characteristic so as to permit linemen to climb the poles safely and easily through ready gaff penetration. The water tends to locate between the cellulose fibers by hydrogen bonds giving the fibers more flexibility and making them less crystalline in nature.

We have determined that when the oil percentage gets significantly below 5, there is a reduction in the moisture retention characteristic of the wood. It has also been found that when the oil percentage goes substantially above 5, the ability to introduce the preservative composition into the wood is slightly impeded.

The oil emulsion will be created using a first surfactant with a particular preferred hydrophilic lipophilic balance (HLB). The HLB of the first surfactant is about 7 to 11 and preferably about 8.5 to 9.5. The lipophilic group of the surfactant molecule is the oil loving or non-polar group.

The second surfactant which will be used in water has an HLB of about 15 to 20 and preferably about 18.5 to 19.5. The hydrophilic group of the surfactant molecule is the water loving or polar group. It has been found that with the first and second surfactants selected in this manner, the resultant surfactant material in the wood preservative composition will have an HLB of about 10 to 13 and preferably about 11 to 12.

It is preferred that the first and second surfactants will be present in a total amount of about 0.3 to 2.5 percent based upon the weight of the final emulsion. Among the preferred surfactants are the nonionic surfactants with ethoxylated alkylphenols, such as ethoxylated nonylphenol, may be beneficially employed in the present invention. It is also preferred that different surfactants be employed in the oil solution and the water solution.

In creating the wood preservative composition of the present invention, a first solution is made from the first surfactant and oil. A second solution consisting of a second surfactant and water is created. These two solutions are then admixed to establish an emulsion into which chromated copper arsenate is introduced to create the wood preservative composition. The chromated copper arsenate may be employed in any desired amount with about 0.1 to 15 percent by weight being the preferred amount.

It has been found that the emulsified particles in the emulsions of the present invention have an average size of about 0.5 to 1.5 microns. This facilitates achieving storage stability of the emulsion for prolonged periods such as in excess of about 15 to 30 days thereby facilitating ease of use of the wood protective material of the present invention in spite of the presence of chromated copper arsenate in the emulsion.

The ethylene oxide group in the preferred ethoxylated nonylphenol surfactants of the present invention which may be represented by the expression $(EO)_n$ wherein n is the mole ratio of the number of moles of ethylene oxide to moles of nonylphenol is selected. In this preferred surfactant the "nonyl" group is the oil loving group and the "ethylene oxide" group is the water loving group. It is preferred that the first surfactant have a mole ratio of less than about 5 and that the second surfactant have a mole ratio of greater than about 15, preferably greater than about 20 and most preferably greater than about 50. A specific material suitable for use as a first surfactant is marketed by GAF under the trade designation IGEPAL CO-430 and a specific material suitable for use as the second surfactant is IGEPAL CO-990.

Another preferred form of surfactant is the ethoxylated alkyl alcohols such as laurel, oleyl and stearyl. Specific examples of those which are suitable are the Brij 30 for the first surfactant and Brij 78 or 98 for the second surfactant. These materials are offered by ICI Chemical.

It has been found that by the use of at least two different surfactants having the properties described herein, stable emulsions may be provided.

The invention may be used in connection with a wide variety of hardwoods, softwoods and wood products. It is particularly advantageous for products which will be employed in potentially adverse conditions such as outdoors. Examples of specific end uses for products to be treated by the invention are utility poles, railroad ties, and building products used for decks, fences, foundations, roofs, boat docks, piers, walls and boardwalks.

While the invention is not limited to use with particular types of woods, it may be employed advantageously with woods such as southern yellow pine, Douglas fir, hem/fir, jack pine, western pine, oak, hickory, maple, pacific fir, spruce, pine and fir.

Emulsions prepared in this manner may be used shortly after preparation or as will generally be advantageous in view of the excellent storage stability of the wood preservative composition may be stored for a period of days and subsequently be impregnated in wood. In this context the present invention may be employed either on raw material or finished wood products, as desired. The emulsion of the present invention may be impregnated into the wood by any desired means. Conventional procedures and equipment may be employed. In general, in the known vacuum/pressure cycle, the wood is dried to less than about 35 to 40 percent moisture, is subjected to the vacuum cycle which serves to remove air from the wood and replace it with treating chemicals followed by a pressure cycle during which the treating chemicals are impregnated into the wood followed by a further vacuum which serves to remove excess treating chemicals. In the practice of the present invention it is preferred to employ a pressure of about 120 to 200 psi. The pressure may advantageously be applied in a pulsing manner in order to resist clogging of the material within the wood cells and thereby enhance efficiency of impregnation. For utility poles, the material being impregnated should be present at a depth of about 3 to 3½ inches.

In order to verify the efficacy of the present invention, tests were performed. In these tests the emulsions were prepared using a laboratory Ross L.A.B. 100 L emulsifier. The ingredients were emulsified for five minutes using the fine screen and at a speed setting of 5.

In performing these tests a visual stability rating system was established in accordance with TABLE 1 which ranks emulsions from bad to good.

TABLE 1

| Rating | Stability Test Description |
|---|---|
| 1 | Oil on Water |
| 2 | Oil/Cream/Water |
| 3 | Cream/Water |
| 4 | Oil/Poor Emulsion/Water |
| 5 | Oil/Emulsion/Water |
| 6 | Oil/Cream/Emulsion |
| 7 | Cream/Emulsion/Water |
| 8 | Slight Oil/Emulsion |
| 9 | Cream/Emulsion |
| 10 | Total Emulsion |

These ratings were applied to the test emulsions after the emulsions had been prepared and allowed to sit in an unagitated state for 10 to 30 days.

Stable emulsions of the invention may also be obtained by mixing the surfactants in the oil portion and then mixing the oil portion with the aqueous CCA. Other mixing procedures will be apparent to those skilled in the art.

EXAMPLE I

A series of tests including the use of ethoxylated alkylphenols and ethoxylated alkyl alcohols as surfactants were performed. In each case, the first identified surfactant or emulsifier was mixed with oil and the second identified surfactant was mixed with water. Subsequently, the oil and water emulsions were admixed and 2.0 percent chromated copper arsenate was added. Ten percent by weight highly refined lube base oil based upon the total weight of the final emulsion was employed. The numbers which appear in parentheses after the individual emulsifiers or surfactants is the weight percent of that constituent based upon the total weight of oil. The IGEPAL emulsifiers are ethoxylated alkylphenols and the Brij emulsifiers are ethoxylated alkyl alcohols.

TABLE 2

| Test No. | Oil-CCA Emulsions with Ethoxylated Emulsifiers (10 Percent Oil/2.0 Percent CCA) | | |
|---|---|---|---|
| | Emulsifier | Combined HLB | Stab. Test |
| 1 | Igepal CO-430(6.0)/Igepal CO-630(4.0) | 10.5 | 2 |
| 2 | Igepal CO-430(4.8)/Igepal CO-630(5.2) | 11.0 | 2 |
| 3 | Igepal CO-430(3.6)/Igepal CO-630(6.4) | 11.5 | 2 |
| 4 | Igepal CO-430(2.4)/Igepal CO-630(7.6) | 12.0 | 2 |
| 5 | Igepal CO-430(6.5)/Igepal CO-730(3.5) | 11.0 | 2 |
| 6 | Igepal CO-430(5.6)/Igepal CO-730(4.4) | 11.5 | 6 |
| 7 | Igepal CO-430(7.8)/Igepal CO-880(3.2) | 11.3 | 8 |
| 8 | Igepal CO-430(7.8)/Igepal CO-990(2.2) | 11.0 | 8 |
| 9 | Igepal CO-430(7.4)/Igepal CO-990(2.7) | 11.5 | 8 |
| 10 | Igepal CO-430(6.9)/Igepal CO-990(3.1) | 11.9 | 7 |
| 11 | Igepal CO-430(6.4)/Igepal CO-990(3.6) | 12.4 | 8 |
| 12 | Igepal CO-430(5.9)/Igepal CO-990(4.1) | 13.0 | 7 |
| 13 | Brij 72(3.7)/Brij 78(6.4) | 11.5 | 6 |
| 14 | Brij 72(1.2)/Brij 76(8.8) | 11.5 | 6 |
| 15 | Brij 30(6.9)/Brij 78(3.2) | 11.5 | 7 |
| 16 | Brij 92(3.8)/Brij 98(6.4) | 11.5 | 6 |
| 17 | Brij 92(1.2)/Brij 96(8.8) | 11.5 | 6 |

TABLE 2-continued

Oil-CCA Emulsions with Ethoxylated Emulsifiers
(10 Percent Oil/2.0 Percent CCA)

| Test No. | Emulsifier | Combined HLB | Stab. Test |
|---|---|---|---|
| 18 | Brij 30(7.3)/Brij 98(3.2) | 11.4 | 7 |

(The numbers in parentheses are the weight percent of surfactant based on oil weight.)

As TABLE 2 shows, the use of Igepal CO-430 which has a mole ratio of 4 resulted in superior levels of emulsion stability in tests 6 through 12 but an unacceptable stability rating of 2 in tests 1 through 5. It is noted that the Igepal CO-630 which was used in tests 1 through 4 has a mole ratio of 9 and the Igepal CO-730 has a mole ratio of 15 while the mole ratio of CO-880 is 30 and Igepal CO-990 is 100. As all of the combined HLB's on tests 1 through 12 were in the range of 10 to 13, it would appear that these tests prove that it is desirable to have a large difference between the mole ratios of the two surfactants.

All of the Brij emulsifiers resulted in a combined HLB of approximately 11.5 and had a minimum stability score of 6. The mole ratio of the Brij materials is as follows:

| Brij No. | Mole Ratio |
|---|---|
| 72 | 2 |
| 92 | 2 |
| 30 | 4 |
| 76 | 10 |
| 96 | 10 |
| 78 | 20 |
| 98 | 20 |

They performed in a successful manner.

EXAMPLE II

Tests were performed to determine (a) the relationship between percentage of oil in the emulsion and retention of the emulsion in the wood and (b) the relationship between the percentage of oil and the rate of moisture loss of the wood. Blocks of Southern yellow pine were used which were cubic in shape and three-quarters of an inch on each side. The chromated copper arsenate was maintained at 2 percent and the emulsifier level maintained at 10 percent of the oil. The emulsifiers used were ethoxylated nonylphenols which were Igepal CO-430 having a mole ratio of 4 and Igepal CO-990 having a mole ratio of 100 and were used respectively in the oil and water. The resulting HLB was 11.5. Impregnation treatments were performed using a vacuum desiccator. The blocks were placed in 250 ml. beakers and weighed. The blocks were covered with the emulsions and a vacuum of 27 inches of mercury was applied. The vacuum was maintained for 30 minutes and followed by 60 minutes at atmospheric pressure. The emulsion retentions were calculated in pounds of emulsion per cubic foot of wood (pcf). The results of this test are given in TABLE 3.

TABLE 3

| Percent Oil in Emulsion Versus Retention | |
|---|---|
| Oil in Emulsion, % | Retention, pcf |
| 10 | 19.7 |
| 7 | 22.6 |
| 5 | 24.1 |
| 3 | 25.8 |
| 2 | 26.0 |
| 1 | 26.1 |
| 0 | 26.0 |

As the lower percentage of emulsion the better the treatment efficiency, it appears that beyond 5 percent oil, there is a reduction in the amount of emulsion retained by the wood.

These blocks were allowed to dry under atmospheric conditions and weighed periodically to obtain a measure of the amount of moisture loss, i.e. drying rate as related to time. The moisture loss tended to follow first order kinetics. The first order rate constants are shown in TABLE 4.

TABLE 4

| Rate of Drying Versus Oil Content in the Emulsion | |
|---|---|
| Percent Oil in Emulsion | Rate Constant, $hr^{-1}$ |
| 10 | 0.0132 |
| 7 | 0.0127 |
| 5 | 0.0124 |
| 3 | 0.0152 |
| 2 | 0.0168 |
| 1 | 0.0164 |
| 0 | 0.0211 |

As it is desirable to maintain some moisture within wood particularly for such uses as utility poles in order to enhance climbability, the lower numbers are preferred. It will be noted that the lowest drying rates appear around 5 percent oil. As a result, not only does use of oil in the neighborhood of 5 percent improve emulsion retention which is an indication of treatability of the wood by the emulsion, but also maintains moisture in the wood which is desirable particularly in terms of utility poles as it enhances climbability. In addition, the cost of the use of additional quantities of oil is eliminated.

EXAMPLE III

EP toxicity tests were performed so as to compare two compositions of the present invention with a commercial formulation. Southern yellow pine was treated with both 5 percent oil and 10 percent oil solutions of the present invention using the Igepal CO-430 and Igepal CO-990 emulsifiers having a combined HLB of 11.5. Also tested was commercially available chromium copper arsenate-Southern yellow pine sawdust samples. The samples of the invention were prepared by treating ¾ inch Southern yellow pine blocks with 1.19 percent CCA. All the blocks were placed in a sealed container above water for two weeks to simulate air drying of larger pieces. Then the blocks were dried in the atmosphere and subsequently ground in a Wiley mill. The CCA oxide retention was calculated to be 0.47 pcf. The test results are shown in TABLE 5.

TABLE 5

| EP Toxicity Test for Oil-CCA Emulsion | | | |
|---|---|---|---|
| | Leachables, ppm | | |
| Sample | Cr | Cu | As |
| 5% Oil-CCA | 3 | 2 | 5 |
| 10% Oil-CCA | 3 | 1 | 4 |

TABLE 5-continued

EP Toxicity Test for Oil-CCA Emulsion

| Sample | Leachables, ppm | | |
|---|---|---|---|
| | Cr | Cu | As |
| Commercial CCA | 7 | 3 | 8 |

It will be appreciated that in categories of chromium, copper and arsenic the two samples of the invention were in all instances less than the commercial wood product. The compositions of the invention, therefore, have improved leach resistance and conductivity as fewer ions are present.

While it will be appreciated that the preferred embodiments of the invention employ non-ionic surfactants, anionic or cationic surfactants may be employed.

Among the advantages of the present invention are that the composition resists undesired oxidation by the chromium (VI) in the chromated copper arsenate. Another advantage of the invention is that workability of the wood such as through sawing, drilling and nailing as well as general workability, is improved. In addition, the invention provides for resistance to splitting, warping and checking through retention of proper moisture content and when used in such products as utility poles, provides improved climbability. All of this and the numerous other benefits set forth herein are produced through the use of an emulsion established through a combination of at least two specifically selected surfactants or emulsifiers in creating respective oil and water emulsions which are admixed prior to addition of the chromated copper arsenate.

It will be appreciated that in the interest of simplicity of disclosure, primary emphasis has been placed on the use of two surfactants. This should be regarded as a minimum and additional surfactants may be employed if desired.

EXAMPLE IV

Certain western species of wood are known to be refractory or difficult to treat with CCA wood preservative chemicals. For these species ammoniacal copper arsenate (ACA) is frequently employed to achieve improved preservative penetration. Experiments were performed to examine the use of ACA-oil emulsion treatment on several of these western species.

In accordance with the American Wood-Preservers' Association Standard P5-86, a 13.5 weight percent ACA concentrate was prepared by dissolving 844 g copper(II) sulfate pentahydrate in 1391 g 29 weight percent aqueous ammonia and 287 g water. To this solution 446 g 75 weight percent arsenic acid and 1031 g of water were added.

An oil-ACA emulsion was prepared by adding a mixture of Igepal CO-430 and CO-990 (combined HLB =11.5) to a highly refined oil. This oil-surfactant solution was emulsified into an ACA solution such that the resulting emulsion contained the components shown in TABLE 6.

TABLE 6

| Component | Weight Percent |
|---|---|
| ACA | 2.0 |
| Oil | 5.0 |
| Emulsifier | 0.5 (based on total solution weight) |

Similarly, a 2.0 weight percent ACA solution was prepared without oil. Twenty-two inch long pieces of Douglas-fir, hem-fir, and white pine, which were end sealed, were treated in pans with both the ACA solution and the ACA-oil emulsion. The treating cycle used was as shown in TABLE 7.

TABLE 7

| | Time, mins. |
|---|---|
| Vacuum, 26" Hg | 15 |
| Pressure, 170 psig | 60 |
| Atmospheric | <5 |

The solution and emulsion retentions for each species were as shown in TABLE 8.

TABLE 8

| Wood Species | Retention, pcf | |
|---|---|---|
| | ACA Solution | ACA-Oil Emulsion |
| Douglas-fir | 4.2 | 2.3 |
| Hem-fir | 33.3 | 14.4 |
| White Pine | 12.1 | 5.8 |

Although the retentions for the emulsion treated wood were about half those of the solution, these retentions should be adequate for preservation. Similar results would be expected for ammoniacal copper zinc arsenate (ACZA).

An important improvement in the appearance of the ACA-oil emulsion treated wood resulted. ACA treated wood normally has a "blotchy", blue-white appearance. However, the ACA-oil emulsion treated wood has a uniform greenish-brown color, similar to CCA treated wood.

If desired, a number of additives for providing advantageous additional properties may be employed. For example, an antifoaming agent may be employed to improve the characteristics of the emulsion. Such an agent, if employed, would typically be introduced in an amount of about 0.01 to 1.0 percent and more preferably about 0.05 to 0.15 percent based upon weight percent for the final emulsion product. A suitable antifoam agent is that marketed by Calgon under the trade designation EC210.

A coloring agent such as a dye or pigment may be employed to impart desired appearance characteristics to the processed wood product. In general, employing an oil soluble dye will result in a more stable emulsion as these are more readily dissolved and are not as heavy as pigment. Pigment formulations can be developed employing standard techniques.

It also may be desirable to add materials such as a fire retardant material and/or an insecticide to the emulsion. Borates, for example, could be incorporated, if desired. Also, additives to impart woodpecker repellency may be incorporated.

Whereas particular embodiments of the invention have been described above for purposes of illustration, it will be evident to those skilled in the art that numerous variations of the details may be made without departing from the invention as defined in the appended claims.

We claim:

1. An improved wood preservative composition of the type comprising an emulsion of oil in a water solution of wood preservative, wherein the oil is from 1 to 20 weight percent of the emulsion, wherein the water contains from 0.1 to 15 weight percent based on emulsion of a wood preservative selected from the group consisting of chromated copper arsenate, ammoniacal copper arsenate and ammoniacal copper zinc arsenate and wherein the composition contains from 0.3 to 2.5 weight percent of the emulsion of a surfactant material; wherein the improvement comprises the surfactant material consisting essentially of a first surfactant having an HLB of from 7 to 11 and a second surfactant having an HLB of from 15 to 20 and the combined HLB of the first and second surfactants being from 10 to 13 and wherein the surfactant is stable in acid solutions.

2. The wood preservative composition of claim 1 wherein the oil is a highly refined oil selected from the group consisting of naphthenic oil, paraffinic oil, number 2 fuel oil, mineral oil and lubricating oil.

3. The wood preservative composition of claim 1 wherein the wood preservative is chromated copper arsenate.

4. The wood preservative composition of claim 1 wherein the oil is present in an amount of from 1 to 6 weight percent.

5. The wood preservative composition of claim 1 wherein the first surfactant has an HLB of from 8.5 to 9.5.

6. The wood preservative composition of claim 1 wherein the second surfactant has an HLB of from 18.5 to 19.5.

7. The wood preservative composition of claim 1 wherein the first surfactant has an HLB of from 8.5 to 9.5, the second surfactant has an HLB of from 18.5 to 19.5 and the combined HLB is from 11 to 12.

8. The wood preservative composition of claim 1 wherein the surfactants are non ionic surfactants.

9. The wood preservative composition of claim 7 wherein the surfactants are non ionic surfactants.

10. The wood preservative composition of claim 9 wherein the oil is present in an amount of from 1 to 6 weight percent.

11. The wood preservative composition of claim 10 wherein the oil is a highly refined oil selected from the group consisting of naphthenic oil, paraffinic oil, number 2 fuel oil, mineral oil and lubricating oil and wherein the wood preservative is chromated copper arsenate.

12. An improved wood preservative composition of the type comprising an emulsion of oil in a water solution of wood preservative wherein the oil is from 1 to 20 weight percent of the emulsion, wherein the water contains from 0.1 to 15 weight percent based on emulsion of a wood preservative selected from the group consisting of chromated copper arsenate, ammoniacal copper arsenate and ammoniacal copper zinc arsenate and wherein the composition contains from 0.3 to 2.5 weight percent of the emulsion of a surfactant material; wherein the improvement comprises a surfactant material consisting essentially of a first surfactant having an HLB of from 7 to 11 selected from ethoxylated alkyl phenols and ethoxylated alkyl alcohols having a mole ratio of ethoxy groups of from 1 to 5, and a second surfactant having an HLB of from 15 to 20 selected from ethoxylated alkyl phenols and ethoxylated alkyl alcohols having a mole ratio of ethoxy groups greater than 20 and the combined HLB of the first and second surfactants being from 10 to 13.

13. The wood preservative composition of claim 12 wherein the wood preservative is chromated copper arsenate.

14. The wood preservative composition of claim 12 wherein the oil is a highly refined oil selected from the group consisting of naphthenic oil, paraffinic oil, number 2 fuel oil, mineral oil and lubricating oil.

15. The wood preservative of claim 12 wherein the first surfactant has an HLB of from 8.5 to 9.5, the second surfactant has an HLB of from 18.5 to 19.5 and the combined HLB is from 11 to 12.

16. The wood preservative of claim 12 wherein the second surfactant has a mole ratio of ethoxy groups greater than 50.

17. The wood preservative composition of claim 15 wherein the oil is present in an amount of from 1 to 6 weight percent.

18. The wood preservative composition of claim 17 wherein the wood preservative is chromated copper arsenate and the oil is a highly refined oil selected from the group consisting of naphthenic oil, paraffinic oil, number 2 fuel oil, mineral oil and lubricating oil.

* * * * *